US006527981B1

(12) United States Patent
Tseng et al.

(10) Patent No.: US 6,527,981 B1
(45) Date of Patent: Mar. 4, 2003

(54) AZOLE/AMINE OXIDE PRESERVATIVES

(75) Inventors: Chuen-ing Tseng, Lawrenceville, NJ (US); Leigh E. Walker, Macungie, PA (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/578,015

(22) Filed: May 24, 2000

Related U.S. Application Data

(60) Provisional application No. 60/135,562, filed on May 24, 1999.

(51) Int. Cl.$^7$ ................................................. C09K 3/00
(52) U.S. Cl. ...................... 252/384; 428/541; 428/907; 106/18.32
(58) Field of Search .................. 252/384; 428/541, 428/907; 106/18.32

(56) References Cited

U.S. PATENT DOCUMENTS

| | | | |
|---|---|---|---|
| 3,296,145 A | 1/1967 | Findlan et al. ............. 252/106 |
| 3,484,523 A | 12/1969 | Findlan et al. ............. 424/248 |
| 3,658,985 A | * 4/1972 | Olson ......................... 424/70 |
| 3,761,488 A | 9/1973 | Lewis et al. ................ 260/302 |
| 4,005,193 A | 1/1977 | Green et al. ................ 424/168 |
| 4,105,431 A | 8/1978 | Lewis et al. .................. 71/67 |
| 4,379,810 A | 4/1983 | Amundsen et al. ......... 428/541 |
| 4,382,105 A | 5/1983 | Amundsen et al. ......... 427/370 |
| 4,526,699 A | 7/1985 | Jones et al. .................. 252/99 |
| 4,622,248 A | 11/1986 | Leach et al. ................ 427/440 |
| 4,857,322 A | 8/1989 | Goettsche et al. .......... 424/633 |
| 4,888,349 A | * 12/1989 | Brandes ...................... 514/383 |
| 4,929,454 A | 5/1990 | Findlay et al. .............. 424/638 |
| 4,937,143 A | 6/1990 | West ........................ 427/419.8 |
| 4,950,685 A | 8/1990 | Ward ........................ 514/479 |
| 4,961,878 A | * 10/1990 | Mullins .................... 252/389.3 |
| 5,073,570 A | 12/1991 | Tseng ........................ 514/533 |
| 5,276,029 A | 1/1994 | Goettsche et al. ........ 514/231.2 |
| 5,304,237 A | 4/1994 | Barth et al. ................ 106/18.3 |
| 5,426,121 A | 6/1995 | Bell ............................ 514/500 |
| 5,468,284 A | 11/1995 | Sturm ........................... 106/2 |
| 5,486,315 A | 1/1996 | Tseng ........................ 252/547 |
| 5,500,153 A | 3/1996 | Figueroa et al. ............ 252/548 |
| 5,527,384 A | 6/1996 | Williams et al. ......... 106/18.32 |
| 5,536,505 A | 7/1996 | Yu ........................... 106/18.33 |
| H1635 H | 3/1997 | Vander Meer ............. 510/220 |
| 5,833,741 A | 11/1998 | Walker ........................ 106/2 |
| 5,858,921 A | 1/1999 | Magin et al. ............... 504/206 |
| 5,891,836 A | 4/1999 | Kacher ....................... 510/237 |
| 5,922,672 A | 7/1999 | Stringer et al. ............. 510/503 |
| 5,929,016 A | 7/1999 | Harrison .................... 510/384 |
| 6,037,316 A | 3/2000 | Garner et al. .............. 510/238 |
| 6,075,030 A | * 6/2000 | Wagner ...................... 514/275 |
| 6,080,715 A | 6/2000 | Bianchi et al. ............. 510/444 |
| 6,159,924 A | 12/2000 | Weller et al. ............... 510/384 |
| 6,180,672 B1 | 1/2001 | Lichtenberg et al. ....... 514/561 |
| 6,395,698 B1 | 5/2002 | Daun et al. ................. 510/384 |
| 6,416,789 B1 | 7/2002 | Marks et al. ............... 424/641 |

FOREIGN PATENT DOCUMENTS

| | | | |
|---|---|---|---|
| CA | 1 174 005 | 9/1984 | ......... A01N/31/14 |
| DE | 3743 821 A1 | 7/1989 | ............ B27K/3/34 |
| DE | 4217 882 A1 | 12/1993 | ......... A01N/55/04 |
| DE | 44 41 674 A1 | 5/1996 | ......... C07C/275/32 |
| DE | 196 40 874 | 4/1998 | ............ B27K/3/34 |
| DE | 196 48 888 A1 | 5/1998 | ............ B27K/3/50 |
| EP | 0 370 182 | 5/1990 | ............ B27K/3/50 |
| EP | 0 381 482 | 8/1990 | ............ B27K/3/50 |
| EP | 0 571 846 A1 | 12/1993 | ......... A01N/47/12 |
| JP | 57022003 | 2/1982 | ............ B27K/3/52 |
| JP | 64-1796 | 1/1989 | ............ C11D/3/28 |
| JP | 1-268605 | 10/1989 | ......... A01N/33/24 |
| JP | 9059672 | 3/1997 | |
| WO | 97/01423 | 1/1997 | ............ B27K/3/50 |
| WO | 98/00008 | 1/1998 | ......... A01N/25/02 |
| WO | 98/18321 | 5/1998 | ......... A01N/25/30 |
| WO | 98/31518 | 7/1998 | ............ B27K/3/00 |
| WO | WO-9833381 A1 * | 8/1998 | |

OTHER PUBLICATIONS

American Wood Preservers' Association, P5–Waterborne Preservatives, 4–5, 1998.
Encyclopedia of Chemical Technology, vol 2, pp. 259–271, John Wiley & Sons Inc., 1978.
Archer et al., Forest Products Journal, 45(1):86–89, Jan. 1995.
Hirobumi et al., 120:301698 1993 (abstract).
Liu et al., 25$^{th}$ Annual Meeting of the International Research Group on Wood Preservation, Nusa Dua Bali, Indonesia, May 29, 1994–Jun. 3, 1994.
Nicholas et al., 28$^{th}$ Annual Meeting of the International Research Group on Wood Preservation, Whistler, Canada, May 25, 1997–May 30, 1997.
Williams et al., American Wood–Perservers' Association, 90:156–176, 1994.

* cited by examiner

Primary Examiner—Cephia D. Toomer
(74) Attorney, Agent, or Firm—Darby & Darby

(57) ABSTRACT

Applicants have discovered that amine oxides enhance the performance of azoles as fungicides and wood preservatives. Also, amine oxides have been found to provide waterproofing properties and enhance the uniform distribution and penetration of azoles into wood substrates. The present invention provides a composition comprising an amine oxide and an azole, such as a 1,2,4-triazole. The composition of the present invention may be incorporated into or be a wood preservative and waterproofing system, or agricultural product. Another embodiment of the present invention is a method for preserving and/or waterproofing a wood substrate by applying the composition to the wood substrate. Yet another embodiment is an article comprising a wood substrate and the composition of the present invention. The invention also provides a method of controlling fungi comprising applying an effective amount of the composition of the present invention to the fungi or the area on which the fungi grow.

34 Claims, No Drawings ated groups.azoles:dimethyl"

AZOLE/AMINE OXIDE PRESERVATIVES

This application claims the benefit of U.S. Ser. No. 60/135,562, filed May 24, 1999.

FIELD OF THE INVENTION

This invention relates to compositions containing an azole and an amine oxide and their use as wood preservative and waterproofing compositions and as fungicides in agricultural products.

BACKGROUND OF THE INVENTION

Azoles are generally known to be effective as wood preservatives. Azole compounds are registered with the US Environmental Protection Agency (EPA) for use in wood protection treatment to buildings, forest products, finished wood products, log houses, wooden aquatic structures, wooden containers, and pressure treated forest products. Azoles are also used in industrial preservation applications and agriculture applications to protect plants, fruits, vegetables, cereal crops and sugar corps from fungal attack.

Azole compounds are lipophilic, due to their organic nature, and have good solubility in organic medium. However, they typically have poor solubility in aqueous solutions. According to "The Pesticide Manual, $11^{th}$ Edition", C. D. S. Tomlin, editor, published by the British Crop Protection Council, UK (1997), the solubility of propiconazole in water is 100 ppm at 20° C., and that of tebuconazole in water is 36 ppm at 20° C. A number of wood preservation concentrates have recently been developed to circumvent the water solubility problem.

DE 19648888 describes water-thinned wood preservative concentrates containing at least 5% triazole fungicide in an aqueous benzalkonium halide solution, e.g., a 50% aqueous ($C_{12-14}$ alkyl)benzyldimethyl ammonium chloride solution.

WO 98/18321 describes a microbicide microemulsion containing a solvating surfactant selected from alkoxylated castor oil, alkoxylated hydrogenated castor oil and an alkyoxylated rosin.

WO 98/00008 describes a liquid pesticidal composition containing azole compounds in an organic solvent and as surfactants (a) a castor oil ethoxylate having 30–50 mole ethoxylate, (b) a branched $C_8-C_{18}$ alcohol ethoxylate having 5–10 mole ethoxylate, and (c) a tristyrene phenol ethoxylate having 8–30 mole ethoxylate or its phosphate or salt.

DE 4441672 describes wood preservative compositions containing a dimethylalkylamine, an aliphatic $C_8-C_{20}$ dicarboxylic acid, propylene glycol and a triazole compound.

There is a continuing need for improved azole wood preservative and waterproofing compositions and azole antifungal compositions.

SUMMARY OF THE INVENTION

Applicants have discovered that amine oxides enhance the performance of azoles as fungicides and wood preservatives. Also, amine oxides have been found to provide waterproofing properties and enhance the uniform distribution and penetration of azoles into wood substrates. The present invention provides a composition comprising an amine oxide and an azole, such as a 1,2,4-triazole. The composition of the present invention may be incorporated into or be a wood preservative and waterproofing system, or agricultural product.

Another embodiment of the present invention is a method for preserving and/or waterproofing a wood substrate by applying the composition to the wood substrate.

Yet another embodiment is an article comprising a wood substrate and the composition of the present invention.

The invention also provides a method of controlling fungi comprising applying an effective amount of the composition of the present invention to the fungi or the area on which the fungi grow.

DETAILED DESCRIPTION OF THE INVENTION

The present invention provides a composition comprising an amine oxide and an azole. Surprisingly, the fungicidal activity of the azole/amine oxide composition is substantially greater than the sum of the fungicidal activities of the amine oxides and azole separately.

The amine oxide also enhances the uniform distribution and penetration of the azole into wood substrates and improves leach resistance. Furthermore, the azole compositions of the present invention have high water solubility and low volatility.

The compositions of the present invention are useful as wood preservatives for protecting wood from staining, discoloring, molding, rotting and losing its mechanical properties. Wood products which can be preserved with the composition include, but are not limited to, timber, lumber, railway tiles, telephone poles, fences, windows and doors, plywood, particle board, oriented-strained board, chipboard, joinery, bridges and wood products which are generally used in houses, building, construction and carpentry.

The compositions are also useful in textile fibers, e.g., cotton and wool natural fibers and polyamide and polyester synthetic fibers; coatings, e.g., oil paints, dispersion paint, lacquers, and finishing stains; and adhesives and other materials which are degradable by fungi. The compositions may also advantageously be applied in the cellulose and paper industry, in particular to protect pulpwood for paper manufacture from fungal attack.

Additionally, the compositions are useful for industrial preservation to protect products from microbiological attack or degradation, which reduces or destroys their economic value. Examples of such products include, but are not limited to, latexes, adhesives, cellulose products, metal working fluids, coatings, and paint compositions.

The compositions of the present invention are effective against a broad range of fungi. Examples of such fungi include, but are not limited to, Ascomycetes (e.g., Venturia, Podosphaera, Erysiphe, Monilinia, Uncinula, Aureobasidium, Sclerophoma); Basidiomycetes (e.g., Hemileia, Rhizoctonia, Puccinia, Coniophora, Serpula, Poria, Uromyces, Gloeophyllum, Lentinus, Coriolus, Irpex); and fungi imperfecti (e.g., Botrytis, Helminthosporium, Rhynchosporium, Fusarium, Septoria, Cercospora, Alternaria, Pyricularia, Penicillium, Geotrichum).

The amine oxide may be a trialiphatic substituted amine oxide, an N-alkylated cyclic amine oxide, a dialkylpiperazine di-N-oxide, an alkyldi(poly(oxyalkylene))amine oxide, a dialkylbenzylamine oxide, a fatty amidopropyldimethyl amine oxide, a diamine oxide; a triamine oxide, or any combination of any of the foregoing. Preferably, the amine oxide includes at least one $C_8-C_{18}$ alkyl moiety.

Preferred trialiphatic substituted amine oxides have the formula $R^1R^2R^3N\rightarrow O$, where $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups. $R^1$, $R^2$, and $R^3$ independently may be alkyl, alkenyl, or alkynyl groups. More preferably, $R^1$ is a linear, branched, cyclic or any combination thereof $C_8$ to $C_{22}$ saturated or unsaturated group, such as coco, hydrogenated tallow, soya, decyl, hexadecyl, and oleyl; and $R^2$ and $R^3$ independently are linear, branched, or any combination thereof $C_1$ to $C_{22}$ saturated or unsaturated groups, such as coco, hydrogenated tallow, soya, decyl, and hexadecyl.

A preferred trialiphatic substituted amine oxide is a dialkylmethylamine oxide having the formula $R^1R^2CH_3N \rightarrow O$, where $R^1$ and $R^2$ are defined as above. Another preferred trialiphatic substituted amine oxide is an alkyldimethylamine oxide having the formula $R^1(CH_3)_2N \rightarrow O$, where $R^1$ is defined as above. More preferred alkyldimethylamine oxides have the formula $R^{19}(CH_3)_2N \rightarrow O$, where $R^{19}$ is a linear or branched $C_8$–$C_{18}$ alkyl or alkenyl. Preferably, $R^{19}$ is a linear or branched $C_8$–$C_{16}$ alkyl. Alkyldimethylamine oxides are non-toxic and non-mutagenic surfactants. Suitable alkyldimethylamine oxides include, but are not limited to, a $C_{10}$ alkyldimethylamine oxide, a $C_{10}$–$C_{14}$ alkyldimethylamine oxide, a $C_{12}$–$C_{16}$ alkyldimethylamine oxide, a $C_{16}$–$C_{18}$ alkyldimethylamine oxide, and any combination of any of the foregoing.

Preferred N-alkylated cyclicamine oxides have the formula $R^4R^5R^6N \rightarrow O$ where $R^4$ is defined as $R^1$ above and $R^5$ and $R^6$ are linked to form a cyclic group. The cyclic group typically contains from 4 to 10 carbon atoms and may optionally contain oxygen, sulfur, nitrogen, or any combination of any of the foregoing. More preferred N-alkylated cyclicamine oxides include, but are not limited to, an alkylmorpholine N-oxide, a dialkylpiperazine di-N-oxide, and any combination of any of the foregoing.

Preferred alkylmorpholine N-oxides have the formula

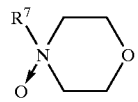

where $R^7$ is defined as $R^1$ above. According to a more preferred embodiment, $R^7$ is a linear or branched $C_8$ to $C_{16}$ alkyl. Examples of preferred alkylmorpholine N-oxides include, but are not limited to, cetyl morpholine N-oxide and lauryl morpholine N-oxide.

Preferred dialkylpiperazine di-N-oxides have the formula

where $R^8$ is defined as $R^1$ above and $R^9$ is defined as $R^2$ above.

Preferred alkyldi(poly(oxyalkylene))amine oxides have the formula

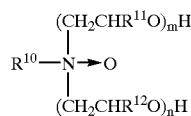

where $R^{10}$ is defined as $R^1$ above; $R^{11}$ and $R^{12}$ independently are H or $CH_3$; and m and n independently are integers from about 1 to about 10.

Preferred dialkylbenzylamine oxides have the formula $R^{13}R^{14}R^{15}N \rightarrow O$, where $R^{13}$ is defined as $R^1$ above; $R^{14}$ is defined as $R^2$ above; and $R^{15}$ is benzyl. More preferred dialkylbenzylamine oxides include, but are not limited to, alkylbenzylmethylamine oxides having the formula $R^{13}R^{15}CH_3N \rightarrow O$ where $R^{13}$ and $R^{15}$ are defined as above. According to a more preferred embodiment, $R^{13}$ is a linear or branched $C_8$–$C_{12}$ alkyl.

Preferred fatty amidopropyldimethyl amine oxides have the formula

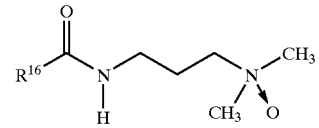

where $R^{16}$ is defined as $R^1$ above.

Preferred diamine oxides have the formula

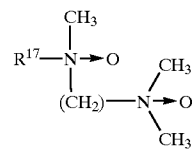

where $R^{17}$ is defined as $R^1$ above; and m is an integer from about 1 to about 10.

Preferred triamine oxides have the formula

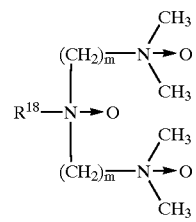

where $R^{18}$ is defined as $R^1$ above; and m and n independently are integers from about 1 to about 10.

Long chain ($C_{16}$ or greater) amine oxides, such as hexadecylamine oxides and hydrogenated tallow amine oxides, are particularly preferable for imparting waterproofing properties to the composition. Short chain ($C_{14}$ and shorter) amine oxides aide in solubilizing the azole and long chain amine oxides.

The azole is preferably a 1,2,4-triazole. Suitable 1,2,4-triazoles include, but are not limited to, triadimefon, triadimenol, triazbutil, propiconazole, cyproconazole, difenoconazole, tebuconazole, myclobutanil, triadimenol, fenbuconazole, etaconazole, bromoconazole, flusiazole, uniconazole, diniconazole, bitertanol, hexaconazole, azaconazole, flutriafol, epoxiconazole, fluquinoconazole, tetraconazole, penconazole, and any combination of any of the foregoing. Preferred azoles include, but are not limited to triadimefon, propiconazole, cyproconazole, tebuconazole, myclobutanil, fenbuconazole, and any combination of any of the foregoing. More preferably, the azole is propiconazole, tebuconazole, or any combination of any of the foregoing. The azole may also be a benzimidazole, such as thiabendazole, benomyl, and carbendazim.

A preferred amine oxide/azole combination is a $C_{10}$–$C_{16}$ alkyl dimethylamine oxide or a mixture of $C_{10}$–$C_{16}$ alkyl dimethylamine oxides with propiconazole, cyproconazole, tebuconazole, or a combination thereof. More preferred $C_{10}$–$C_{16}$ alkyl dimethylamine oxides for these combinations include, but are not limited to, coco-dimethylamine oxide, a mixture of branched $C_{10}$–$C_{14}$ alkyl dimethyl amine oxides, and any combination of any of the foregoing.

The composition may include a solvent, such as water and water miscible solvents, including, but not limited to, alcohols, glycols, esters, ethers, polyethers, amides, and any combination of any of the foregoing.

The weight ratio of amine oxide to azole broadly ranges from about 5000:1 to about 0.1:1 and preferably ranges from about 100:1 to about 1:1. According to one preferred embodiment, the weight ratio ranges from about 40:1 to about 5:1 and is more preferably about 20:1.

According to one embodiment of the invention, the composition in concentrated form contains broadly from about 5 to about 100%, preferably from about 10 to about 50%, and more preferably from about 10 to about 35% by weight of combined amine oxide and azole based upon 100% weight of total composition.

Use dilutions of the composition typically comprise a fungicidally effective amount of azole and amine oxide. Generally, the use dilution comprises a fungicide enhancing effective amount of amine oxide, i.e., an amount of amine oxide sufficient to enhance the fungicidal efficacy of the azole. For wood applications, the use dilution may comprise a wood distribution, penetrating enhancing, waterproofing, and/or fungicide enhancing effective amount of amine oxide and a fungicidally effective amount of azole. Use dilutions preferably comprise from about 0.01 to about 5.0%, more preferably from about 0.1 to about 5.0%, and most preferably from about 0.5 to about 5.0% by weight of amine oxide, based upon 100% weight of total composition. Use dilutions preferably comprise from about 0.00001% (0.1 ppm) to about 2.0%, more preferably from about 0.0001% (1 ppm) to about 1.0%, and most preferably from about 0.0005% (5 ppm) to about 0.5% by weight of azole, based upon 100% weight of total composition.

The composition may be incorporated into or be a wood preservative and/or waterproofing system or an agricultural product.

Other adjuvants may be included in the composition as known to one of ordinary skill in the art. Examples of such adjuvants include, but are not limited to, thickeners, drying oils, anti-oxidants, UV absorbers, pigments, waxes, and any combination of any of the foregoing. Other biocides, fungicides and insecticides may be include in the composition. Any organic insecticide or fungicide that can be solubilized by an aqueous amine oxide solution is suitable for use in the present composition. Suitable insecticides include, but are not limited to, chloropyrifos, folpet, captafol, captan, pyrethroids, and any combination of any of the foregoing. Suitable fungicides include, but are not limited to, iodopropargyl butylcarbamate, tributyltin oxide, 2-(thiocyanomethylthio)benzothiazole, iodo-sulfones, azoles, isothiazalones, and any combination of any of the foregoing.

Another embodiment of the present invention is a method for preserving and/or waterproofing a wood substrate by applying the composition of the present invention to the wood substrate. The composition may be applied to the wood substrate by any method known to one of ordinary skill in the art. For example, the composition may be applied by treating the wood substrate under pressure or vacuum, in a thermal or dip system. Alternatively, it may be applied by a surface treatment, such as brushing, dipping, soaking, and spraying.

The invention also includes a method of controlling fungi comprising applying an effective amount of one or more compositions of the present invention. The term "controlling" as used herein includes, but is not limited to, inhibiting growth of fungi.

The composition of the present invention may be prepared by mixing the azole, amine oxide, solvents, and adjuvants. The mixture may be heated and/or stirred to expedite mixing.

DESCRIPTION OF THE PREFERRED EMBODIMENTS

The following examples illustrate the invention without limitation. All parts and percentages are given by weight unless otherwise indicated.

The abbreviations "DMAO" and "BMAO" in the examples stand for dimethylamine oxide and benzyl methylamine oxide, respectively. The following ingredients were used in the examples:

(a) branched alkyl ($C_{10}$–$C_{14}$) dimethylamine oxide (branched alkyl ($C_{10}$–$C_{14}$) DMAO), which is available as Barlox® 12i from Lonza Inc. of Fair Lawn, N.J.;

(b) coco-alkyl ($C_{12}$–$C_{16}$) dimethylamine oxide (coco-DMAO) which is available as Barlox® 12 from Lonza Inc. of Fair Lawn, N.J.;

(d) octyl dimethylamine oxide (octyl-DMAO), decyl dimethylamine oxide (decyl-DMAO), dodecyldimethylamine oxide (dodecyl-DMAO), tetradecyl dimethylamine oxide (tetradecyl-DMAO), hexadecyl dimethylamine oxide (hexadecyl-DMAO), octadecyl dimethylamine oxide (octadecyl-DMAO), which are available as FMBAO-8™, Barlox® 10S, Barlox® 12S, Barlox® 14, Barlox® 16S, and Barlox® 18S, from Lonza Inc. of Fair Lawn, N.J.;

(e) coco-alkyl-di(hydroxyethyl)amine oxide and tallow-alkyl-di(hydroxyethyl)amine oxide which are available as Aromox™ C/12 and Aromox™T/12 from Akzo Chemical of Chicago, Ill.;

(f) the other amine oxides described below can be prepared from the corresponding amine with hydrogen peroxide according to the procedure described in U.S. Pat. No. 5,486,315, which is herein incorporated by reference;

(g) cyproconazole and propiconazole which are available from Janssen Pharmaceutica of Titusville, N.J.;

(h) fenbuconazole and myclobutanil which are available from Rohm and Haas of Spring House, Pa.; and (i) tebuconazole and triadimefon which are available from Bayer Corporation of Pittsburgh, Pa.

Barlox® 100S, 12, 12i, 14, and 16S are 30% (w/w) aqueous solutions of their corresponding amine oxides. Barlox® 18S and FMBAO-8 are 25% and 40% (w/w) aqueous solutions of their corresponding amine oxides, respectively. Barlox® 10S, 12, 12i, and 14 and FMBAO-8 are liquids. Barlox® 16S and 18S are a viscous liquid and a paste, respectively.

EXAMPLE 1

1.06 g of propiconazole was dissolved in 16.88 g of 31.4% (w/w) coco-DMAO in water with stirring to form a solution containing about 29.5% by weight of coco-DMAO and about 5.89% by weight of propiconazole. The weight ratio of coco-DMAO to propiconazole was about 5:1.

3.39 g of the propiconazole/coco-DMAO solution having a weight ratio of about 5:1 was diluted with 96.61 g of water to form a clear solution containing about 1% by weight of coco-DMAO and about 0.05 g by weight of propiocnazole.

0.45 g of propiconazole was dissolved in 28.66 g of 31.4% (w/w) coco-DMAO (in water) and 15.86 g of water with stirring to form a clear solution containing about 20% by weight of coco-DMAO and 1% by weight of propiconazole. The weight ratio of coco-DMAO to propiconazole was about 20:1.

5.00 g of the propiconazole/coco-DMAO solution having a weight ratio of about 20:1 was diluted with 95 g of water to form a clear solution containing about 1% by weight of coco-DMAO and about 0.05% by weight of propiconazole.

EXAMPLE 2

The procedure in Example 1 was repeated except that branched alkyl ($C_{10}$–$C_{14}$) DMAO was substitued for coco-DMAO.

EXAMPLE 3

1.06 g of tebuconazole was dissolved in 16.86 g of 31.4% (w/w) coco-DMAO in water with heating to from about 40 to about 50° C. and stirring to form a clear, colorless solution containing about 29.5% by weight of coco-DMAO and about 5.89% by weight of tebuconazole. The weight ratio of coco-DMAO to tebuconazole was about 5:1.

0.45 g of tebuconazole was dissolved in 28.66 g of 31.4% (w/w) coco-DMAO (in water) and 15.86 g of water with heating to from about 40 to about 50° C. and stirring to form a clear solution containing about 20% by weight of coco-DMAO and 1% by weight of tebuconazole. The weight ratio of coco-DMAO to tebuconazole was about 20:1. 5.00 g of the tebuconazole/coco-DMAO solution having a weight ratio of about 20:1 was diluted with 95 g of water to form a clear solution containing about 1% by weight of coco-DMAO and 0.05% by weight of tebuconazole.

EXAMPLE 4

The procedure in Example 3 was repeated except that triadimefon was substituted for tebuconazole.

EXAMPLE 5

20.0 g of dodecyl-DMAO in solid form (95% purity) was mixed well with 1.0 g of tebuconazole powder to obtain a solid white mixture.

1.05 g of the tebucoanzole/dodecyl-DMAO mixture was added to 98.95 g of water to form a clear, colorless solution containing about 1% by weight of dodecyl-DMAO and about 0.05% by weight of tebuconazole.

EXAMPLE 6

The procedure in Example 1 was repeated with the azoles and amine oxides in the amounts specified in Table 1 below. The solubility of the azoles in the solution is shown in Table

TABLE 1

Solubility of Azoles in Amine Oxides

| Azole | Amine Oxide | % by weight of Azole | % by weight of Amine Oxide | Soluble |
|---|---|---|---|---|
| Cyproconazole | Coco-DMAO | 5.00 | 28.50 | Yes |
| Fenbuconazole | | 1.00 | 29.70 | Yes |
| Myclobutanil | | 5.00 | 28.50 | Yes |
| Propiconazole | | 5.00 | 28.50 | Yes |

TABLE 1-continued

Solubility of Azoles in Amine Oxides

| Azole | Amine Oxide | % by weight of Azole | % by weight of Amine Oxide | Soluble |
|---|---|---|---|---|
| Tebuconazole | | 3.00 | 29.10 | Yes |
| Triadimefon | | 2.50 | 29.25 | Yes |
| Cyproconazole | Branched Alkyl | 5.00 | 28.50 | Yes |
| Fenbuconazole | ($C_{10}$–$C_{14}$)-DMAO | 1.00 | 29.70 | Yes |
| Myclobutanil | | 5.00 | 28.50 | Yes |
| Propiconazole | | 5.00 | 28.50 | Yes |
| Tebuconazole | | 3.00 | 29.10 | Yes |
| Triadimefon | | 2.50 | 29.25 | Yes |
| Cyproconazole | Decyl-DMAO | 5.00 | 28.50 | Yes |
| Fenbuconazole | | 1.00 | 29.70 | Yes |
| Myclobutanil | | 5.00 | 28.50 | Yes |
| Propiconazole | | 5.00 | 28.50 | Yes |
| Tebuconazole | | 5.00 | 29.10 | Yes |
| Triadimefon | | 2.50 | 29.63 | Yes |

COMPARATIVE EXAMPLE 6A

The solubility of propiconazole, tebuconazole, and triadimefon (without amine oxide) in water is shown in Table 2 below. "The Pesticide Manual, 11$^{th}$ Edition", C. D. S. Tomlin, editor, published by The British Crop Protection Council, UK (1997).

TABLE 2

| Azole | Appearance | Solubility in water[a] | Solubility in Water[b] |
|---|---|---|---|
| Cyproconazole | White Powder | 140 ppm/25° C. | 140 ppm at 22° C. |
| Fenbuconazole | Off-White Powder | 0.2 ppm/25° C. | 4 ppm at 25° C. |
| Myclobutanil | Off-White Powder | 142 ppm/25° C. | 142 ppm at 25° C. |
| Propiconazole | Brown Oil | 100 ppm/20° C. | 100 ppm at 20° C. |
| Tebuconazole | White Powder | 36 ppm/20° C. | 32 ppm at 20° C. |
| Triadimefon | White Powder | 64 ppm/20° C. | 64 ppm at 20° C. |

[a]"The Pesticide Manual, 11$^{th}$ Edition", C.D.S. Tomlin, editor, published by The British Crop Protection Council, UK (1997).
[b]Material Safety Data Sheet of respective azoles.
[c]Also found in Bayer Technical Information Sheet No. N-107, Bayer Corporation of Pittsburgh, PA.

COMPARATIVE EXAMPLE 6B

Aqueous mixtures containing 1% by weight of propiconazole and 20% by weight of 4-methyl morpholine-N-oxide, pyridine N-oxide, trimethylamine oxide, or dimethylbenzylamine oxide were prepared. The weight ratio of amine oxide to propiconazole in each solution was about 20:1. In all the solutions, the propiconazole was not soluble in the solution and oiled out at the bottom of the flask.

EXAMPLE 7

A composition solution containing 5.0% by weight of propiconazole and 95% by weight of Barlox® 12 was prepared. Barlox® 12 is an aqueous solution containing 30% by weight of coco-DMAO. This composition was stored at room temperature for 13 months. NMR spectroscopy was used to analyze the sample. No decomposition of the composition was observed.

A composition solution containing 5.0% by weight of tebuconazole and 95% by weight of Barlox® 12 was prepared. This composition was stored at room temperature for 1 year. No decomposition of the composition was observed.

EXAMPLE 8

The corrosivity of the aqueous azole/amine oxide solutions in Table 3 was determined as follows. Approximately 20 mL of each aqueous test solution was prepared containing 1% by weight of amine oxide and 0.05% by weight of azole. The test solution was added to a Wheaton borosilicate glass scintillation vial having a polyethylene screw cap. A ½"×1½"×0.032" low carbon steel coupon with a ¼" hole punched ¼" from the top edge, available from Q-Panel Company of Cleveland, Ohio, was suspended from the cap via teflon coated clips. After suspension, the bottom edge of the coupon was approximately ¹⁄₁₆" to ³⁄₃₂" above the bottom of the vial. The coupon was immersed in the solution and stored at room temperature. The coupon was observed for signs of corrosion after 24 hours, 2 weeks, and 24 days.

The results are shown in Table 3 below.

TABLE 3

| Amine Oxide | Azole | Initial Solution | Observation after 24 Hours | Observation after 14 Days | Observation after 24 Days |
|---|---|---|---|---|---|
| Octyl-DMAO | Propiconazole | Clear, Colorless Solution | No Corrosion | No Corrosion | No Corrosion |
| Decyl-DMAO | Propiconazole | Clear, Colorless Solution | No Corrosion | No Corrosion | Slight Edge Corrosion |
| Dodecyl-DMAO | Propiconazole | Clear, Colorless Solution | No Corrosion | No Corrosion | No Corrosion |
| Branched Alkyl ($C_{10}$–$C_{14}$) DMAO | Propiconazole | Clear, Colorless Solution | No Corrosion | Slight edge corrosion on coupon | Edge Corrosion |
| Coco-DMAO | Propiconazole | Clear, Colorless Solution | No Corrosion | No Corrosion | No Corrosion |
| Hexadecyl-DMAO | Propiconazole | Solution lightly turbid | No Corrosion | No Corrosion | No Corrosion |
| Octadecyl-DMAO | Propiconazole | Turbid Solution | No Corrosion | No Corrosion | No Corrosion |
| Oleyl-DMAO | Propiconazole | Clear, light yellow Solution | No Corrosion | No Corrosion | No Corrosion |
| Dodecylbenzyl methylamine oxide | Propiconazole | Clear, Colorless Solution | No Corrosion | No Corrosion | No Corrosion |
| Cetyl morpholine N-oxide | Propiconazole | Clear, Colorless Solution | No Corrosion | No Corrosion | No Corrosion |
| Branched Alkyl ($C_{10}$–$C_{14}$) DMAO | Tebuconazole | Clear, Colorless Solution | No Corrosion | No Corrosion | No Corrosion |
| Coco-DMAO | Tebuconazole | Clear, Colorless Solution | No Corrosion | No Corrosion | No Corrosion |
| Coco-DMAO | Triadimefon | Clear, Colorless Solution | No Corrosion | No Corrosion | No Corrosion |

COMPARATIVE EXAMPLE 8A

The corrosivity of the solutions in Table 4 was determined by the procedure described in Example 8. The results are shown in Table 4 below.

TABLE 4

| Solution | Initial Solution | Observation after 24 hours | Observation after 14 Days | Observation after 24 Days |
|---|---|---|---|---|
| De-ionized water | Clear, Colorless Solution | Coupon has black surface | Solution rusty and coupon rust colored | Solution rusty and coupon rust colored |
| 1% by weight of NP-1 Sapstain Control Chemical ™[1] | Turbid | Rusty, Orange precipitation | Rusty, Orange precipitation | Rusty, Orange precipitation |
| 1% by weight of didecyldimethyl ammonium chloride[2] | Clear, Colorless Solution | Black corrosion | Black precipitation, corrosion on coupon surface | Black precipitation, corrosion on coupon surface |
| 1% by weight of | Blue, clear | Rust | Rust | Rust precipitation, |

TABLE 4-continued

| Solution | Initial Solution | Observation after 24 hours | Observation after 14 Days | Observation after 24 Days |
|---|---|---|---|---|
| ammoniated copper quat, type D[3] | solution | precipitation | precipitation, corrosion on coupon edge | corrosion on coupon edge |
| 1% by weight of alkyl ($C_{12}$–$C_{16}$) benzyldimethyl ammonium chloride[4] | Clear, light yellow Solution | Coupon surface black | Coupon surface black, rust precipitation | Coupon surface black, rust precipitation |
| 1% by weight of didecyl dimethyl ammonium carbonate[5] | Clear, Colorless Solution | No Corrosion | No Corrosion | No Corrosion |

[1]NP-1 Sapstain Control Chemical ™ is available from Kop-Coat Inc. of Pittsburgh, PA.
[2]Didecyldimethyl ammonium chloride is available as Bardac 2280 from Lonza Inc.
[3]Ammoniated copper quat, type D, is available from Chemical Specialties, Inc. of Charlotte, NC. It is prepared following the procedure described in "American Wood-Preservers' Association Standard", published by American Wood Preservers Association, pages 12–13 (1999).
[4]Alkyl ($C_{12}$–$C_{16}$) benzyldimethyl ammonium chloride is available as Barquat 80–28 from Lonza Inc.
[5]Didecyldimethyl ammonium carbonate can be prepared according to the procedure described in WO 94/28715.

EXAMPLE 9

The corrosivity of the aqueous azole/amine oxide solutions in Table 5 on aluminum was determined as follows. Approximately 40 mL of each aqueous test solution was prepared containing 1% by weight of amine oxide and 0.05% by weight of azole. The test solution was added to a 8-dram borosilicate glass vial (25 mm outer diameter×95 mm height, 32 mL) having a polyethylene screw cap. A 3"×½"×1/16" aluminum coupon with a ¼" hole punched ¼" from the top edge and having a 120 grit surface, available from Metal Samples Co. of Munford, Ala., was suspended from the cap via teflon coated clips. After suspension, the bottom edge of the coupon was approximately 1/16" to 3/32" above the bottom of the vial. The coupon was immersed in the solution and stored at about 50° C. The coupon was observed for signs of corrosion after 2 weeks and 8 months.

The results are shown in Table 5 below.

TABLE 5

| Amine Oxide | Azole | Initial Solution | Observation after 14 Days | Observation after 8 Months |
|---|---|---|---|---|
| Decyl-DMAO | Propiconazole | Clear, Colorless Solution | No Corrosion | No Corrosion |
| Branched alkyl ($C_{10}$–$C_{14}$) DMAO | Propiconazole | Clear, Colorless Solution | No Corrosion | No Corrosion |
| Coco-DMAO | Propiconazole | Clear, Colorless Solution | No Corrosion | No Corrosion |
| Coco-DMAO | Tebuconazole | Clear, Colorless Solution | No Corrosion | No Corrosion |
| Coco-DMAO | Triadimefon | Clear, Colorless Solution | No Corrosion | No Corrosion |
| Hexadecyl-DMAO | Propiconazole | Homogeneous, Turbid Solution | No Corrosion | No Corrosion |
| Octadecyl-DMAO | Propiconazole | Homogeneous, Turbid Solution | No Corrosion | No Corrosion |
| Cetyl morpholine N-oxide | Propiconazole | Clear, Colorless Solution | No Corrosion | Solution Clear; Trace Sediments |
| Oleyl-DMAO | Propiconazole | Clear, Light Yellow Solution | No Corrosion | No Corrosion |

COMPARATIVE EXAMPLE 9A

The procedure described in Example 9 was repeated with the solutions in Table 8 below. These solutions did not contain any azoles. The results are also shown in Table 6.

TABLE 6

| Solution | Initial Solution | Observation after 14 Days | Observation after 8 Months |
|---|---|---|---|
| De-ionized water | Clear, Colorless Solution | Coupon Corroding, No Sediments | Coupon Corroding, Trace Sediments |
| 1% by weight of | Clear, Colorless | Solution With | Solution With |

TABLE 6-continued

| Solution | Initial Solution | Observation after 14 Days | Observation after 8 Months |
|---|---|---|---|
| didecyldimethyl ammonium chloride[1] | Solution | Sediments | Sediments |
| 1% by weight of ammoniated copper quat, type D[2] | Dark Blue & Clear Solution | Dark Blue and Clear Solution; Sediments; Coupon Corroding | Brown Coupon; White Sediment; Bad Corrosion |
| 1% by weight of didecyldimethyl ammonium carbonate[3] | Clear, Colorless Solution | Hazy Liquid; Lots of Sediment | Hazy Liquid; Lots of Sediment |
| 1% by weight of alkyl ($C_{12}$–$C_{16}$) benzyldimethyl ammonium chloride[4] | Clear, Colorless Solution | No Corrosion | Clear Solution; Trace Sediments |

[1]Didecyldimethyl ammonium chloride is available as Bardac ® 2280 from Lonza Inc.
[2]Ammoniated copper quat, type D, is available from Chemical Specialties, Inc. of Charlotte, NC. It is prepared following the procedure described in "American Wood-Preservers' Association Standard", published by American Wood Preservers Association, pages 12–13 (1999).
[3]Didecyldimethyl ammonium carbonate is prepared according to the procedure described in WO 94/28715.
[4]Alkyl ($C_{12}$–$C_{16}$) benzyldimethyl ammonium chloride is available as Barquat ® 80-28 from Lonza Inc.

EXAMPLE 10

The efficacy of the aqueous amine oxide solutions in Table 7 at various concentrations against the wood rot fungi *T. versicolor* (white rot fungi), *G. trabeum* (brown rot fungi), *P. placenta* (brown rot fungi), and *C. globosum* (soft rot decay fungi) were determined using the agar dilution plate method well known in the art. The minimum concentration of each amine oxide required to achieve 100% growth retardation of each specific organism, i.e., the minimum inhibitory concentration (MIC), was determined. The percent retardation of the fungi was determined by the percentage change in the diameter of the fungi on the agar plate (i.e. Percent Retardation=((Diameter of Control)−(Diameter of Treated Fungi))/(Diameter of Control)*100%).

The results are shown in Table 7 below.

TABLE 7

| | MIC (ppm of amine oxides) | | | |
|---|---|---|---|---|
| Amine Oxide | *T. versicolor* (ppm) | *G. trabeum* (ppm) | *P. placenta* (ppm) | *C. globosum* (ppm) |
| Octyldimethylamine oxide | 750 | 1000 | 1000 | >1000 |
| Decyl-DMAO | 750 | 250 | 500 | >1000 |
| Coco-DMAO | 750 | 500 | 500–1000 | >1000 |
| Branched alkyl ($C_{10}$–$C_{14}$) DMAO | 500 | 250 | 500 | >1000 |
| Dodecyl-DMAO | 250 | 250 | 250 | >1000 |
| Tetradecyl-DMAO | >1000 | >1000 | >1000 | >1000 |
| Hexadecyl-DMAO | >1000 | >1000 | >1000 | >1000 |
| Oleyl-DMAO | >1000 | >1000 | >1000 | >1000 |
| Octadecyl-DMAO | >1000 | >1000 | >1000 | >1000 |
| Behenyl DMAO | >1000 | >1000 | >1000 | >1000 |
| Coco-di(hydroxyethyl)-amine oxide | 500 | 500 | 500 | >1000 |
| Tallow-di(hydroxyethyl)-amine oxide | >1000 | >1000 | >1000 | >1000 |
| Dodecyl-BMAO | >1000 | 1000 | >1000 | >1000 |
| Lauryl morpholine N-oxide | 750 | 1000 | 500 | >1000 |

The minimum concentration of the aqueous amine oxide solutions in Table 8 required to achieve 50% growth retardation of each specific organism, i.e., $IC_{50}$, was estimated from the data obtained using Table2D curve fitting. The results are shown in Table 8.

TABLE 8

| Fungi | Barlox ® 12 | | Barlox ® 12i | | Bardac ® 2280 | |
|---|---|---|---|---|---|---|
| | $IC_{50}$ (ppm) | MIC (ppm) | $IC_{50}$ (ppm) | MIC (ppm) | $IC_{50}$ (ppm) | MIC (ppm) |
| T. versicolor | 51 | 750 | 84 | 500 | 28 | >1000 |
| G. trabeum | 9 | 500 | 44 | 250 | 8 | >1000 |
| P. placenta | 5 | 1000 | 89 | 500 | <5 | 1000 |
| C. globosum | 47 | >1000 | 153 | >1000 | 28 | >1000 |

Barlox ® 12 is an aqueous solution containing 30% by weight of coco-DMAO.
Barlox ® 12i is an aqueous solution containing 30% by weight of branched ($C_{10}$–$C_{14}$) alkyl-DMAO.
Bardac ® 2280 is an 80% (w/w) aqueous solution of didecyldimethyl ammonium chloride and is available as Bardac 2280 from Lonza Inc.

The $IC_{50}$ and MIC concentrations in Tables 7 and 8 above are in ppm of amine oxides and didecyldimethyl ammonium chloride.

EXAMPLE 11

The efficacy of the aqueous azole solutions in Table 9 at various concentrations against the wood rot fungi *T. versicolor* (white rot fungi), *G. trabeum* (brown rot fungi), *P. placenta* (brown rot fungi), and *C. globosum* (soft rot decay fungi) were determined using the agar dilution plate method well known in the art. The minimum concentration of each azole required to achieve 100% growth retardation of each specific organism, i.e., the minimum inhibitory concentration (MIC), was determined. The minimum concentration of each azole required to achieve 50% growth retardation of each specific organism, i.e., $IC_{50}$, was estimated from the data obtained using Table2D curve fitting. The percent retardation of the fungi was determined by the percentage change in the diameter of the fungi on the agar plate (i.e. Percent Retardation=((Diameter of Control)−(Diameter of Treated Fungi))/(Diameter of Control)*100%).

The results are shown in Table 9 below.

TABLE 9

| | T. versicolor | | G. trabeum | | P. placenta | | C. globosum | |
|---|---|---|---|---|---|---|---|---|
| Azole | $IC_{50}$ (ppm) | MIC (ppm) | $IC_{50}$ (ppm) | MIC (ppm) | $IC_{50}$ (ppm) | MIC (ppm) | $IC_{50}$ (ppm) | MIC (ppm) |
| Cyproconazole | 0.2 | 2.5 | 0.3 | 2.5 | 0.7 | 2.5 | 2.3 | 25 |
| Fenbuconazole | 1.1 | 25 | 0.3 | 50 | 3.9 | 25 | 10.7 | 50 |
| Myclobutanil | 6 | 50 | 4.3 | >50 | 13 | 50 | — | >50 |
| Propiconazole | 3 | 50 | 0.9 | >50 | 0.7 | 50 | 11.7 | >50 |
| Tebuconazole | 2.3 | 25 | <0.1 | 10 | 1.7 | 50 | 34.5 | 50–500 |

EXAMPLE 12

The efficacy of aqueous propiconazole/amine oxide solutions containing the amine oxides in Table 10 against the wood rot fungi *T. versicolor* (white rot fungi), *G. trabeum* (brown rot fungi), *P. placenta* (brown rot fungi), and *C. globosum* (soft rot decay fungi) were determined using the agar dilution plate method well known in the art. Each solution was tested at dilutions of 0.5, 5, 50, and 250 ppm of propiconazole. The weight ratio of amine oxide to azole was about 20:1 in each solution. The percent retardation of the fungi was determined by the percentage change in the diameter of the fungi on the agar plate (i.e. Percent Retardation=((Diameter of Control)−(Diameter of Treated Fungi))/(Diameter of Control)*100%).

The results are shown in Table 10 below.

TABLE 10

| Amine Oxide | Concentration of Propiconazole (ppm) | Percent Retardation | | | |
|---|---|---|---|---|---|
| | | T. Versicolor | G. trabeum | P. placenta | C. globosum |
| Octyldimethylamine oxide | 250 | 100 | 100 | 100 | 100 |
| | 50 | 100 | 100 | 100 | 100 |
| | 5 | 100 | 89 | 100 | 85 |
| | 0.5 | 11 | 69 | 62 | 42 |
| Decyl-DMAO | 250 | 100 | 100 | 100 | 100 |
| | 50 | 100 | 100 | 100 | 100 |
| | 5 | 100 | 100 | 100 | 81 |
| | 0.5 | 19 | 69 | 71 | 46 |
| Dodecyl-DMAO | 250 | 100 | 100 | 100 | 100 |
| | 50 | 100 | 100 | 100 | 100 |
| | 5 | 100 | 100 | 100 | 81 |
| | 0.5 | 49 | 71 | 69 | 45 |
| Branched alkyl ($C_{10}$–$C_{14}$) DMAO | 250 | 100 | 100 | 100 | 100 |
| | 50 | 100 | 100 | 100 | 100 |
| | 5 | 100 | 100 | 100 | 100 |
| | 0.5 | 29 | 61 | 60 | 48 |
| Coco-DMAO | 250 | 100 | 100 | 100 | 100 |
| | 50 | 100 | 100 | 100 | 90 |
| | 5 | 100 | 100 | 100 | 84 |
| | 0.5 | 13 | 72 | 76 | 52 |
| Tetradecyl-DMAO | 250 | 100 | 100 | 100 | 84 |
| | 50 | 100 | 100 | 100 | 83 |
| | 5 | 87 | 86 | 100 | 80 |
| | 0.5 | 5 | 64 | 73 | 51 |
| Hexadecyl-DMAO | 250 | 100 | 100 | 100 | 86 |
| | 50 | 100 | 100 | 100 | 85 |
| | 5 | 89 | 85 | 100 | 81 |
| | 0.5 | 15 | 68 | 81 | 51 |
| Octadecyl-DMAO | 250 | 100 | 100 | 100 | 97 |
| | 50 | 100 | 100 | 100 | 89 |
| | 5 | 91 | 85 | 100 | 77 |
| | 0.5 | 16 | 61 | 60 | 48 |
| Oleyl-DMAO | 250 | 100 | 100 | 100 | 83 |
| | 50 | 100 | 86 | 100 | 83 |
| | 5 | 90 | 83 | 100 | 70 |
| | 0.5 | 50 | 59 | 63 | 31 |
| Behenyl-DMAO | 250 | 100 | 100 | 100 | 97 |
| | 50 | 100 | 100 | 100 | 88 |
| | 5 | 86 | 85 | 100 | 73 |
| | 0.5 | 11 | 61 | 55 | 42 |
| Coco-di(hydroxyethyl) amine oxide | 250 | 100 | 100 | 100 | 100 |
| | 50 | 100 | 100 | 100 | 88 |
| | 5 | 100 | 86 | 100 | 71 |
| | 0.5 | 19 | 68 | 61 | 44 |
| Tallow-di(hydroxyethyl)amine oxide | 250 | 100 | 100 | 100 | 87 |
| | 50 | 100 | 87 | 100 | 86 |
| | 5 | 100 | 85 | 100 | 76 |
| | 0.5 | 28 | 67 | 65 | 51 |
| Cetyl morpholine N-oxide | 250 | 100 | 100 | 100 | 86 |
| | 50 | 100 | 100 | 100 | 84 |
| | 5 | 87 | 81 | 100 | 63 |
| | 0.5 | 16 | 62 | 69 | 4 |
| Didodecyl methyl amine oxide | 250 | 100 | 100 | 100 | 100 |
| | 50 | 100 | 100 | 100 | 81 |
| | 5 | 94 | 84 | 100 | 71 |
| | 0.5 | 14 | 58 | 74 | 43 |
| Dodecyl-BMAO | 250 | 100 | 100 | 100 | 97 |
| | 50 | 100 | 100 | 100 | 90 |
| | 5 | 88 | 82 | 100 | 71 |
| | 0.5 | 36 | 68 | 64 | 41 |
| Lauryl morpholine N-oxide | 250 | 100 | 100 | 100 | 100 |
| | 50 | 100 | 100 | 100 | 85 |
| | 5 | 100 | 84 | 100 | 66 |
| | 0.5 | 34 | 68 | 72 | 30 |
| Octyl-BMAO | 250 | 100 | 100 | 100 | 97 |
| | 50 | 100 | 100 | 100 | 100 |
| | 5 | 100 | 100 | 100 | 88 |
| | 0.5 | 13 | 67 | 65 | 48 |
| Didecyldimethyl ammonium chloride (Bardac ® 2280) | 250 | 100 | 100 | 100 | 100 |
| | 50 | 100 | 100 | 100 | 86 |
| | 5 | 100 | 82 | 100 | 80 |

TABLE 10-continued

| Amine Oxide | Concentration of Propiconazole (ppm) | Percent Retardation | | | |
|---|---|---|---|---|---|
| | | T. Versicolor | G. trabeum | P. placenta | C. globosum |
| | 0.5 | 39 | 68 | 83 | 66 |
| — | 250 | 100 | 100 | 100 | 100 |
| (Bardap ® 26) | 50 | 100 | 100 | 100 | 86 |
| | 5 | 100 | 76 | 100 | 83 |
| | 0.5 | 40 | 70 | 81 | 65 |

EXAMPLE 13

The procedure described in Example 12 was repeated with the aqueous tebuconazole/amine oxide solutions in Table 11.

The results are shown in Table 11 below.

TABLE 11

| Amine Oxide | Concentration of Tebuconazole (ppm) | Percent Retardation | | | |
|---|---|---|---|---|---|
| | | T. Versicolor | G. trabeum | P. placenta | C. globosum |
| Octyldimethylamine oxide | 250 | 100 | 100 | 100 | 100 |
| | 50 | 100 | 100 | 100 | 100 |
| | 5 | 100 | 100 | 100 | 56 |
| | 0.5 | 81 | 76 | 47 | 28 |
| Decyl-DMAO | 250 | 100 | 100 | 100 | 100 |
| | 50 | 100 | 100 | 100 | 100 |
| | 5 | 100 | 100 | 100 | 58 |
| | 0.5 | 81 | 82 | 57 | 22 |
| Dodecyl DMAO | 250 | 100 | 100 | 100 | 100 |
| | 50 | 100 | 100 | 100 | 83 |
| | 5 | 100 | 100 | 100 | 70 |
| | 0.5 | 67 | 84 | 71 | 15 |
| Branched alkyl ($C_{10}$–$C_{14}$) DMAO | 250 | 100 | 100 | 100 | 100 |
| | 50 | 100 | 100 | 100 | 100 |
| | 5 | 100 | 100 | 100 | 74 |
| | 0.5 | 70 | 83 | 43 | −7 |
| Coco-DMAO | 250 | 100 | 100 | 100 | 100 |
| | 50 | 100 | 100 | 100 | 79 |
| | 5 | 100 | 100 | 100 | 63 |
| | 0.5 | 62 | 86 | 72 | 23 |
| Tetradecyl-DMAO | 250 | 100 | 100 | 100 | 78 |
| | 50 | 100 | 100 | 100 | 76 |
| | 5 | 100 | 100 | 100 | 58 |
| | 0.5 | 20 | 81 | 72 | 29 |
| Hexadecyl-DMAO | 250 | 100 | 100 | 100 | 83 |
| | 50 | 100 | 100 | 100 | 81 |
| | 5 | 100 | 100 | 100 | 44 |
| | 0.5 | 65 | 85 | 72 | 33 |
| Octadecyl-DMAO | 250 | 100 | 100 | 100 | 100 |
| | 50 | 100 | 100 | 100 | 82 |
| | 5 | 100 | 100 | 100 | 3 |
| | 0.5 | 58 | 78 | 51 | 21 |
| Oleyl-DMAO | 250 | 100 | 100 | 100 | 79 |
| | 50 | 95 | 100 | 100 | 74 |
| | 5 | 88 | 100 | 100 | 51 |
| | 0.5 | 48 | 82 | 56 | 34 |
| Behenyl-DMAO | 250 | 100 | 100 | 100 | 100 |
| | 50 | 100 | 100 | 100 | 82 |
| | 5 | 100 | 100 | 100 | −8 |
| | 0.5 | 58 | 82 | 47 | −26 |
| Tallow-di(hydroxyethyl)amine oxide | 250 | 100 | 100 | 100 | 78 |
| | 50 | 100 | 100 | 100 | 78 |
| | 5 | 86 | 100 | 100 | 45 |
| | 0.5 | 46 | 85 | 70 | 25 |
| Cetyl morpholine N-oxide | 250 | 100 | 100 | 100 | 76 |
| | 50 | 100 | 100 | 100 | 74 |
| | 5 | 100 | 100 | 100 | 51 |
| | 0.5 | 71 | 83 | 69 | 10 |
| Dodecyl-BMAO | 250 | 100 | 100 | 100 | 77 |

TABLE 11-continued

| Amine Oxide | Concentration of Tebuconazole (ppm) | Percent Retardation | | | |
|---|---|---|---|---|---|
| | | T. Versicolor | G. trabeum | P. placenta | C. globosum |
| | 50 | 100 | 100 | 100 | 76 |
| | 5 | 93 | 100 | 100 | 56 |
| | 0.5 | 56 | 84 | 68 | 21 |
| Lauryl morpholine N-oxide | 250 | 100 | 100 | 100 | 100 |
| | 50 | 100 | 100 | 100 | 82 |
| | 5 | 100 | 100 | 100 | 57 |
| | 0.5 | 65 | 84 | 73 | 8 |
| Octyl-BMAO | 250 | 100 | 100 | 100 | 100 |
| | 50 | 100 | 100 | 100 | 100 |
| | 5 | 95 | 100 | 100 | 53 |
| | 0.5 | 17 | 79 | 54 | 1 |

EXAMPLE 14

The procedure described in Example 12 was repeated with the aqueous cyproconazole/amine oxide solutions in Table 12.

The results are shown in Table 12 below.

TABLE 12

| Amine Oxide | Concentration of Cyproconazole (ppm) | Percent Retardation | | | |
|---|---|---|---|---|---|
| | | T. Versicolor | G. trabeum | P. placenta | C. globosum |
| Coco-DMAO | 50 | 100 | 100 | 100 | 100 |
| | 25 | 100 | 100 | 100 | 100 |
| | 5 | 100 | 100 | 100 | 74 |
| | 0.5 | 26 | 73 | 24 | 17 |

EXAMPLE 15

The procedure described in Example 12 was repeated with the aqueous fenbuconazole/amine oxide solutions in Table 13.

The results are shown in Table 13 below.

TABLE 13

| Amine Oxide | Concentration of Fenbuconazole (ppm) | Percent Retardation | | | |
|---|---|---|---|---|---|
| | | T. Versicolor | G. trabeum | P. placenta | C. globosum |
| Coco-DMAO | 100 | 100 | 100 | 100 | 100 |
| | 50 | 100 | 100 | 100 | 100 |
| | 5 | 100 | 100 | 100 | 73 |
| | 0.5 | 49 | 77 | 65 | 40 |

EXAMPLE 16

The procedure described in Example 11 was repeated with the aqueous myclobutanil/amine oxide solutions in Table 14. The results are shown in Table 16 below.

TABLE 14

| Amine Oxide | Concentration of Myclobutanil (ppm) | Percent Retardation | | | |
|---|---|---|---|---|---|
| | | T. Versicolor | G. trabeum | P. placenta | C. globosum |
| Coco-DMAO | 100 | 100 | 100 | 100 | 86 |
| | 50 | 100 | 100 | 100 | 84 |
| | 5 | 100 | 100 | 100 | 64 |
| | 0.5 | 75 | 74 | 62 | 26 |

EXAMPLE 17

The procedure described in Example 11 was repeated with the aqueous triadimefon/amine oxide solutions in Table 15.

The results are shown in Table 15 below.

TABLE 15

| Amine Oxide | Concentration of Triadimefon (ppm) | Percent Retardation | | | |
|---|---|---|---|---|---|
| | | T. Versicolor | G. trabeum | P. placenta | C. globosum |
| Octyl-DMAO | 250 | 100 | 100 | 100 | 100 |
| | 50 | 100 | 100 | 100 | 80 |
| | 5 | 90 | 86 | 100 | 56 |
| | 0.5 | 21 | 73 | 45 | 17 |
| Coco-DMAO | 250 | 100 | 100 | 100 | 88 |
| | 50 | 100 | 100 | 100 | 75 |
| | 5 | 100 | 100 | 100 | 53 |
| | 0.5 | 21 | 76 | 59 | 16 |
| Branched alkyl ($C_{10}$–$C_{14}$) DMAO | 250 | 100 | 100 | 100 | 100 |
| | 50 | 100 | 100 | 100 | 100 |
| | 5 | 100 | 100 | 100 | 40 |
| | 0.5 | 18 | 62 | 36 | −17 |
| Hexadecyl-DMAO | 250 | 100 | 100 | 100 | 77 |
| | 50 | 100 | 100 | 100 | 69 |
| | 5 | 89 | 85 | 100 | 56 |
| | 0.5 | 20 | 71 | 71 | 41 |
| Cetyl morpholine N-oxide | 250 | 100 | 100 | 100 | 72 |
| | 50 | 100 | 100 | 100 | 69 |
| | 5 | 100 | 87 | 100 | 36 |
| | 0.5 | 15 | 57 | 54 | 13 |

EXAMPLE 18

Synergism for the aqueous propiconazole/amine oxide solutions in Table 16 against *T. Versicolor* and *G. trabeum* were calculated by the methods described in C. E. Kull et al., "Mixtures of Quaternary Ammonium Compounds and Long-chain Fatty Acids as Antifungal Agents", *Applied Microbiology*, 9:538–541 (1961). The synergism value ($Q_A/Q_a+Q_B/Q_b$) was determined. $Q_A$ is the concentration of amine oxide (in ppm) in an amine oxide/azole mixture, which yielded 100% retardation of a specific wood rot organism. $Q_a$ is the concentration of amine oxide alone (in ppm) required to yield 100% retardation of a specific wood rot organism. $Q_B$ is the concentration of azole (in ppm) in an amine oxide/azole mixture, which yielded 100% retardation of a specific wood rot organism. $Q_b$ is the concentration of azole alone (in ppm) required to yield 100% retardation of a specific wood rot organism. All of the amine oxide/azole solutions in Table 19 exhibited 100% retardation of the specified wood rot organism.

When the value of ($Q_A/Q_a+Q_B/Q_b$) is less than one, the mixture is synergistic. Values for ($Q_A/Q_a+Q_B/Q_b$) of 1 and greater than 1, represent an additive effect and an antagonistic effect, respectively.

$Q_a$ for coco-DMAO, decyl-DMAO, branched alkyl ($C_{10}$–$C_{14}$)-DMAO, and dodecyl-DMAO against *T. versicolor* were determined to be 750, 750, 500, and 250 ppm, respectively. $Q_a$ for coco-DMAO, decyl-DMAO, branched alkyl ($C_{10}$–$C_{14}$)-DMAO, and dodecyl-DMAO against *G. Trabeum* were determined to be 500, 250, 250, and 250 ppm, respectively. $Q_a$ for decyl-DMAO, branched alkyl ($C_{10}$–$C_{14}$)-DMAO, and dodecyl-DMAO against *P. placenta* were determined to be 500,500, and 250 ppm, respectively. $Q_b$ for propiconazole against *T. versicolor, G. trabeum*, and *P. placenta* were all determined to be 50 ppm.

TABLE 16

| Amine Oxide | Concentration of Amine Oxide (ppm) | Concentration of Propiconazole (ppm) | $Q_A/Q_a + Q_B/Q_b$ (for *T. vesicolor*) | $Q_A/Q_a + Q_B/Q_b$ (for *G. trabeum*) |
|---|---|---|---|---|
| Coco-DMAO | 250 | 2.5 | 0.38 | 0.55 |
| | 250 | 0.5 | 0.34 | 0.51 |
| | 200 | 5 | 0.37 | 0.50 |
| | 200 | 1 | 0.29 | 0.42 |
| | 125 | 5 | 0.27 | 0.35 |
| | 125 | 2.5 | 0.22 | 0.30 |
| | 50 | 10 | 0.27 | 0.30 |
| | 50 | 0.5 | 0.08 | 0.11 |
| | 25 | 10 | 0.23 | 0.25 |
| | 25 | 5 | 0.13 | 0.15 |
| | 25 | 2.5 | 0.08 | 0.10 |
| | 12.5 | 2.5 | 0.07 | 0.08 |
| | 10 | 25 | 0.51 | 0.52 |
| | 5 | 25 | 0.51 | 0.51 |
| Decyl-DMAO | 100 | 5 | 0.23 | 0.5 |
| Branched Alkyl ($C_{10}$–$C_{14}$)-DMAO | 100 | 5 | 0.30 | 0.5 |
| Dodecyl-DMAO | 100 | 5 | 0.50 | 0.5 |

The aqueous propiconazole/amine oxide solutions in Table 17 below were tested against *P. placenta*. The results are shown in Table 17 below.

TABLE 17

| Amine Oxide | Concentration of Amine Oxide (ppm) | Concentration of Propiconazole (ppm) | $Q_A/Q_a + Q_B/Q_b$ (for *P. Placenta*) |
|---|---|---|---|
| Decyl-DMAO | 100 | 5 | 0.3 |
| Branched Alkyl ($C_{10}$–$C_{14}$)-DMAO | 100 | 5 | 0.3 |
| Dodecyl-DMAO | 100 | 5 | 0.5 |

EXAMPLE 19

The procedure described in Example 18 was repeated for the aqueous tebuconazole/amine oxide solutions in Tables 18 and 19. The results are shown in Tables 18 and 19.

$Q_a$ for coco-DMAO, branched alkyl ($C_{10}$–$C_{14}$)-DMAO, decyl-DMAO, dodecyl-DMAO, tetradecyl-DMAO, hexadecyl-DMAO, octadecyl-DMAO, behenyl-DMAO, octyl-DMAO, and lauryl morpholine N-oxide against *T. versicolor* were determined to be 750, 500, 750, 250, 1000, 1000, 1000, 1000, 750, and 750. $Q_a$ for coco-DMAO, branched alkyl ($C_{10}$–$C_{14}$)-DMAO, decyl-DMAO, and dodecyl-DMAO against *G. trabeum* were determined to be 500,250, 250, and 250 ppm, respectively and $Q_a$ for tetradecyl-DMAO, hexadecyl-DMAO, octadecyl-DMAO, behenyl-DMAO, octyl-DMAO, and lauryl morpholine N-oxide were all determined to be 1000 ppm. $Q_a$ for decyl-DMAO, dodecyl-DMAO, and lauryl morpholine N-oxide against *P. placenta* were determined to be 500, 250, and 500 ppm, respectively, and $Q_a$ for tetradecyl-DMAO, hexadecyl-DMAO, octadecyl-DMAO, behenyl-DMAO, and octyl-DMAO were all determined to be 1000 ppm. $Q_b$ for tebuconazole against *T. versicolor, G. trabeum*, and *P. placenta* were determined to be 25, 10, and 50 ppm, respectively.

TABLE 18

| Amine Oxide | Concentration of Amine Oxide (ppm) | Concentration of Tebuconazole (ppm) | $Q_A/Q_a + Q_B/Q_b$ (for T. vesicolor) | $Q_A/Q_a + Q_B/Q_b$ (for G. trabeum) |
|---|---|---|---|---|
| Coco-DMAO | 500 | 0.1 | 0.67 | 1.01 |
| | 200 | 1 | 0.31 | 0.50 |
| | 125 | 5 | 0.37 | 0.75 |
| | 100 | 5 | 0.33 | 0.70 |
| | 100 | 1 | 0.17 | 0.30 |
| | 10 | 10 | 0.41 | 1.02 |
| | 5 | 5 | 0.21 | 0.51 |
| | 0.5 | 5 | 0.20 | 0.50 |
| Branched Alkyl ($C_{10}$–$C_{14}$)-DMAO | 250 | 0.25 | 0.51 | 1.03 |
| | 125 | 5 | 0.45 | 1.00 |
| | 100 | 5 | 0.40 | 0.90 |
| | 100 | 1 | 0.24 | 0.50 |
| | 25 | 1 | 0.09 | 0.20 |
| | 10 | 10 | 0.42 | 1.04 |
| | 5 | 5 | 0.21 | 0.52 |
| | 2.5 | 2.5 | 0.11 | 0.26 |
| Decyl-DMAO | 100 | 5 | 0.33 | 0.9 |
| Dodecyl-DMAO | 100 | 5 | 0.60 | 0.9 |
| Tetradecyl-DMAO | 100 | 5 | 0.30 | 0.6 |
| Hexadecyl-DMAO | 100 | 5 | 0.30 | 0.6 |
| Octadecyl-DMAO | 100 | 5 | 0.30 | 0.6 |
| Behenyl-DMAO | 100 | 5 | 0.30 | 0.6 |
| Octyl-DMAO | 100 | 5 | 0.33 | 0.6 |
| Lauryl morpholine N-oxide | 100 | 5 | 0.33 | 0.6 |

The aqueous solutions in Table 19 below were tested against *P. placenta*. The results are shown in Table 19 below.

TABLE 19

| Amine Oxide | Concentration of Amine Oxide (ppm) | Concentration of Tebuconazole (ppm) | $Q_A/Q_a + Q_B/Q_b$ (for P. Placenta) |
|---|---|---|---|
| Decyl-DMAO | 100 | 5 | 0.3 |
| Dodecyl-DMAO | 100 | 5 | 0.5 |
| Tetradecyl-DMAO | 100 | 5 | 0.2 |
| Hexadecyl-DMAO | 100 | 5 | 0.2 |
| Octadecyl-DMAO | 100 | 5 | 0.2 |
| Behenyl-DMAO | 100 | 5 | 0.2 |
| Octyl-DMAO | 100 | 5 | 0.2 |
| Lauryl morpholine N-oxide | 100 | 5 | 0.3 |

EXAMPLE 20

The efficacy of the aqueous azole/amine oxide solutions in Table 20 were tested by the procedure described in Example 12. All of these compositions exhibited 100% retardation of *T. versicolor*, *G. trabeum*, and *P. placenta*.

TABLE 20

| Amine Oxide | Azole | Concentration of Amine Oxide (ppm) | Concentration of Azole (ppm) |
|---|---|---|---|
| Coco-DMAO | Triadimefon | 100 | 5 |
| Branched Alkyl ($C_{10}$–$C_{14}$)-DMAO | Triadimefon | 100 | 5 |
| Cetyl morpholine N-oxide | Tebuconazole | 100 | 5 |
| Octylbenzylmethyl amine oxide | Propiconazole | 100 | 5 |

EXAMPLE 21

The waterproofing efficacy of the azole/amine oxide solutions in Table 21 on ponderosa pine end-grain wafers (5"×0.75"×0.25") was determined as follows. The sample wafers were equilibrated at ambient conditions before treating and were weighed. The samples were then placed in a vacuum desiccator equipped with an addition funnel and evacuated to a pressure (vacuum) of 0.1 atmosphere for 15 minutes. The treating solution was added to the sample and the pressure in the desiccator increased to atmospheric. The samples were allowed to remain in the solution for five minutes, then removed, blotted, and allowed to air dry to constant weight.

The samples were weighed and immersed in deionized water for about 30 minutes. The samples were removed, surface water was blotted and the samples were weighed and the weight percent of water absorbed was calculated for each sample.

Waterproofing ability is judged by the amount of water that is absorbed by a wooden specimen on immersion for a given time in water. Waterproofing index numbers (WR Index) were calculated by comparing a treated sample with a matched untreated control specimen using the following equation:

$$\text{WR Index} = \frac{[\% \text{ Uptake Untreated Control} - \% \text{ Uptake Treated Sample}]}{\% \text{ Uptake Untreated Control}} \times 100$$

positive index number indicates a degree of waterproofing for the composition. Higher numbers are better than low numbers. A formulation that totally prevents water absorption would have a rating of 100. For certain millwork applications, an index of 60 is required.

The results are shown in Table 21 below.

TABLE 21

| No. | Amine Oxide | Azole | Weight Ratio of Amine Oxide to Azole | % Water Uptake | WR Index |
|---|---|---|---|---|---|
| 1 | Coco-DMAO | Propiconazole | 20 | 26.65 | 56 |
| 2 | Branched alkyl ($C_{10}$–$C_{13}$) DMAO | Propiconazole | 20 | 28.64 | 53 |
| 3 | Tetradecyl-DMAO | Propiconazole | 20 | 31.70 | 48 |
| 4 | Hexadecyl-DMAO | Propiconazole | 20 | 14.49 | 76 |
| 5* | Octadecyl-DMAO | Propiconazole | 20 | 14.68 | 76 |
| 6* | Behenyl-DMAO | Propiconazole | 20 | 13.09 | 79 |
| 7 | Dodecylbenzylmethyl amine oxide | Propiconazole | 20 | 34.81 | 43 |
| 8 | Tallow-di(hydroxyethyl) amine oxide | Propiconazole | 20 | 15.97 | 74 |
| 9 | Didecyldimethylammonium chloride (control) | Propiconazole | 20 | 39.22 | 36 |
| 10 | Cetyl morpholine N-oxide | Propiconazole | 20 | 26.41 | 57 |
| 11 | Oleyl-DMAO | Propiconazole | 20 | 31.15 | 49 |
| 12* | Didecylmethyl amine oxide | Propiconazole | 20 | 21.76 | 64 |
| 13 | Hexadecyl-DMAO | Tebuconazole | 20 | 16.16 | 74 |
| 14* | Octadecyl-DMAO | Tebuconazole | 20 | 16.91 | 72 |
| 15* | Behenyl-DMAO | Tebuconazole | 20 | 11.92 | 80 |
| 16 | Tallow-di(hydroxyethyl) amine oxide | Tebuconazole | 20 | 17.14 | 72 |
| 17 | Cetyl morpholine N-oxide | Tebuconazole | 20 | 24.25 | 60 |
| 18 | Oleyl-DMAO | Tebuconazole | 20 | 31.62 | 48 |
| 19 | Hexadecyl-DMAO | Triadimefon | 20 | 17.59 | 71 |
| 20* | Octadecyl-DMAO | Triadimefon | 20 | 17.81 | 71 |
| 21 | Cetyl morpholine N-oxide | Triadimefon | 20 | 17.09 | 72 |
| 22* | Didodecylpiperazine di-N-oxide | Triadimefon | 20 | 23.99 | 61 |
| 23 | Deionized Water (Control) | None | N/A | 61.00 | N/A |

*The solution is milky.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A composition comprising a synergistic mixture of:

(a) a fungicide enhancing effective amount of one or more amine oxides selected from a group consisting of:

(i) a trialiphatic substituted amine oxide having the formula $R^1R^2R^3N \rightarrow O$, wherein $R^1$ is a linear or branched $C_8$ to $C_{22}$ saturated or unsaturated group; and $R^2$ and $R^3$ are independently linear or branched saturated or unsaturated $C_8$–$C_{22}$ groups;

(ii) an N-alkylated cyclic amine oxide having the formula $R^4R^5R^6N \rightarrow O$, wherein $R^4$ is a linear or branched $C_8$–$C_{40}$ saturated or unsaturated group and $R^5$ and $R^6$ are linked to form a cyclic group;

(iii) a dialkylpiperazine di-N-Oxide having the formula

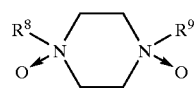

wherein $R^8$ is a linear or branched $C_8$ to $C_{40}$ saturated or unsaturated group; and $R^9$ is a $C_1$ group, linear saturated or unsaturated $C_2$–$C_{40}$ group, or branched saturated or unsaturated $C_3$–$C_{40}$ group;

(iv) an alkyldi(poly(oxyalkylene))amine oxide having the formula

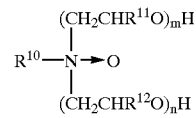

wherein $R^{10}$ is a linear or branched $C_8$ to $C_{40}$ saturated or unsaturated group; $R^{11}$ and $R^{12}$ independently are H or $CH_3$; and m and n independently are integers from about 1 to about 10;

(v) a dialkylbenzylamine oxide having the formula $R^{13}R^{14}R^{15}N \rightarrow O$, wherein $R^{13}$ is a linear or branched $C_8$ to $C_{40}$ saturated or unsaturated group; $R^{14}$ is a $C_1$ group, linear saturated or unsaturated $C_2$–$C_{40}$ group, or branched saturated or unsaturated $C_3$–$C_{40}$ group; and $R^{15}$ is benzyl;

(vi) a fatty amidopropyldimethyl amine oxide having the formula;

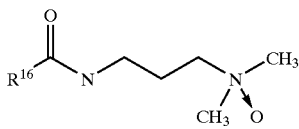

wherein $R^{16}$ is a linear, branched or cyclic $C_8$ to $C_{40}$ saturated or unsaturated group;

(vii) a diamine oxide having the formula

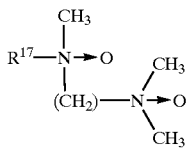

wherein $R^{17}$ is a linear or branched $C_8$ to $C_{40}$ saturated or unsaturated group; and m is an integer from about 1 to about 10;

(viii) a triamine oxide having the formula

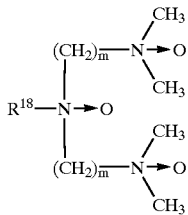

wherein $R^{18}$ is a linear or branched $C_8$ to $C_{40}$ saturated or unsaturated group; and m and n independently are integers from about 1 to about 10; and (ix) any combination of the foregoing; and (b) a fungiciadal effective amount of one or more 1,2,4-triazoles or benzimidazoles.

2. A composition as defined in claim 1, wherein $R^4$ is a linear or branched $C_8$–$C_{22}$ saturated or unsaturated group.

3. A composition as defined in claim 1, wherein the cyclic group of the N-alkylated cyclic amine oxide contains from 4 to 10 carbon atoms.

4. A composition as defined in claim 1, wherein the ring of the cyclic group of the N-alkylated cyclic amine oxide contains oxygen, sulfur, nitrogen, or any combination of any of the foregoing.

5. A composition as defined in claim 1, wherein said N-alkylated cyclicamine oxide is selected from the group consisting of an alkylmorpholine N-oxide, a dialkylpiperazine di-N-oxide, and any combination of any of the foregoing.

6. A composition as defined in claim 5, wherein said alkylmorpholine N-oxide has the formula

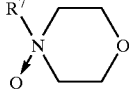

wherein $R^7$ is a linear or branched $C_8$ to $C_{40}$ saturated or unsaturated group.

7. A composition as defined in claim 6, wherein $R^7$ is a linear or branched $C_8$ to $C_{22}$ saturated or unsaturated group.

8. A composition as defined in claim 7, wherein $R^7$ is a linear or branched $C_{10}$ to $C_{16}$ alkyl.

9. A composition as defined in claim 1, wherein $R^8$ is a $C_1$ group, linear saturated or unsaturated $C_2$–$C_{22}$ group, or branched saturated or unsaturated $C_3$–$C_{22}$ group.

10. A composition as defined in claim 1, wherein $R^{10}$ is a linear or branched $C_8$ to $C_{22}$ saturated or unsaturated group.

11. A composition as defined in claim 1, wherein $R^{13}$ is a linear or branched $C_8$ to $C_{22}$ saturated or unsaturated group; and $R^{14}$ is a $C_1$ group, linear saturated or unsaturated $C_2$–$C_{22}$ group, or branched saturated or unsaturated $C_3$–$C_{22}$ group.

12. A composition as defined in claim 1, wherein said dialkylbenzylamine oxide is an alkylbenzylmethylamine oxide having the formula $R^{13}R^{15}CH_3N\rightarrow O$, wherein $R^{13}$ is a linear or branched $C_8$ to $C_{40}$ saturated or unsaturated group; and $R^{15}$ is benzyl.

13. A composition as defined in claim 1, wherein $R^{13}$ is a linear or branched $C_8$ to $C_{22}$ saturated or unsaturated group.

14. A composition as defined in claim 13, wherein $R^{13}$ is a linear or branched $C_8$ to $C_{12}$ saturated or unsaturated group.

15. A composition as defined in claim 1, wherein $R^{16}$ is a linear, branched, cyclic or any combination thereof $C_8$ to $C_{22}$ saturated or unsaturated group.

16. A composition as defined in claim 1, wherein $R^{17}$ is a linear or branched $C_8$ to $C_{22}$ saturated or unsaturated group.

17. A composition as defined in claim 1, wherein $R^{18}$ is a linear or branched $C_8$ to $C_{22}$ saturated or unsaturated group.

18. A composition as defined in claim 1, wherein said 1,2,4-triazole is selected from the group consisting of triadimefon, triazbutil, propiconazole, cyproconazole, difenoconazole, fluquinoconazole, tebuconazole, myclobutanil, triadimenol, fenbuconazole, etaconazole, bromoconazole, flusiazole, uniconazole, diniconazole, bitertanol, hexaconazole, azaconazole, flutriafol, epoxiconazole, tetraconazole, penconazole, and any combination of any of the foregoing.

19. A composition as defined in claim 18, wherein said 1,2,4-triazole is selected from the group consisting of triadimefon, propiconazole, cyproconazole, tebuconazole, myclobutanil, fenbuconazole, and any combination of any of the foregoing.

20. A composition as defined in claim 18, wherein said 1,2,4-triazole is propiconazole.

21. A composition as defined in claim 18, wherein said 1,2,4-triazole is tebuconazole.

22. A composition as defined in claim 1, wherein said benzimidazole is selected from the group consisting of thiabendazole, benomyl, and carbendazim.

23. A composition as defined in claim 1, further comprising a solvent.

24. A composition as defined in claim 23, wherein said solvent is water.

25. A composition as defined in claim 23, wherein said solvent is selected from the group consisting of alcohols, glycols, esters, ethers, polyethers, and any combination of the foregoing.

26. A composition as defined in claim 1, wherein the weight ratio of said amine oxide to said azole ranges from about 100:1 to about 1:1.

27. A composition as defined in claim 26, wherein said weight ratio ranges from about 50:1 to about 5:1.

28. A composition as defined in claim 1, wherein said composition comprises from about 0.1 to about 5% by weight of amine oxide and from about 0.005 to about 0.5% by weight of azole based upon 100% weight of total composition.

29. An article comprising
(A) wood substrate; and
(B) a composition as defined in claim 1.

30. A method of controlling fungi comprising applying an effective amount of one or more compositions of claim 1 to the fungi on an area on which the fungi grow.

31. A composition comprising a synergistic mixture of:
(a) a fungicide enhancing effective amount of one or more trialiphatic substituted amine oxides having the formula $R^1R^2CH_3N{\rightarrow}O$, wherein $R^1$ is a linear or branched $C_8$ to $C_{22}$ saturated or unsaturated group; and $R^2$ is a $C^1$ group, a linear saturated or unsaturated $C_2$–$C_{22}$ group, or branched saturated or unsaturated $C_3$–$C_{22}$ group;
(b) a fungiciadal effective amount of one or more 1,2,4-triazoles selected from the group consisting of triadimefon, triazbutil, propiconazole, cyproconazole, difenoconazole, fluquinconazole, tebuconazole, myclobutanil, triadimenol, fenbuconazole, etaconazole, bromuconazole, flusilazole, uniconazole, diniconazole, bitertanol, hexaconazole, azaconazole, flutriafol, epoxiconazole, tetraconazole, penconazole, and any combination of any of the foregoing,
wherein the weight ratio of amine oxide to 1,2,4-triazole ranges from about 100:1 to about 1:1.

32. A composition as defined in claim 31, wherein said trialiphatic substituted amine oxide is an alkyldimethylamine oxide having the formula $R^1(CH_3)_2N{\rightarrow}O$.

33. A composition as defined in claim 32, wherein $R^1$ is a linear or branched $C_8$–$C_{18}$ saturated or unsaturated group.

34. A composition as defined in claim 33, wherein said alkyldimethylamine oxide is selected from the group consisting of a $C_{10}$ alkyldimethylamine oxide, a mixture of $C_{10}$–$C_{14}$ alkyldimethylamine oxide, a mixture of $C_{16}$–$C_{18}$ alkyldimethylamine oxide, and combination of any of the foregoing.

* * * * *